US00PP19779P2

(12) United States Plant Patent
Danziger

(10) Patent No.: US PP19,779 P2
(45) Date of Patent: Mar. 3, 2009

(54) ***CALIBRACHOA* PLANT NAMED 'DANOA35'**

(50) Latin Name: ***Calibrachoa* sp.**
Varietal Denomination: DANOA35

(76) Inventor: Gabriel Danziger, PO Box 24, Moshav Mishmar Hashiva, Beit Dagan (IL), 50297

( * ) Notice: Subject to any disclaimer, the term of this patent is extended or adjusted under 35 U.S.C. 154(b) by 0 days.

(21) Appl. No.: 12/008,420

(22) Filed: Jan. 11, 2008

(51) Int. Cl.
*A01H 5/00* (2006.01)

(52) U.S. Cl. ..... Plt./413

(58) Field of Classification Search ..... Plt./413, Plt./263

See application file for complete search history.

*Primary Examiner*—Annette H Para
*Assistant Examiner*—S. B. McCormick-Ewoldt

(57) ABSTRACT

A new and distinct *Calibrachoa* cultivar named 'DANOA35' is disclosed, characterized by having cream flowers with distinctive orange veins, a compact, mounded plant habit and continuous flowering. The new variety is a *Calibrachoa*, normally produced as an outdoor garden or container plant.

2 Drawing Sheets

Latin name of the genus and species: *Calibrachoa* sp.
Variety denomination: 'DANOA35'.

BACKGROUND OF THE INVENTION

The new *Calibrachoa* cultivar is a product of a planned breeding program conducted by the inventor, Gabriel Danziger, in Moshav Mishmar Hashiva, Israel. The objective of the breeding program was to produce new *Calibrachoa* varieties for commercial applications. The seed parent is the unpatented, proprietary seedling variety referred to as *Calibrachoa* sp. 'CV-738.' The pollen parent is the unpatented, proprietary seedling variety referred to as *Calibrachoa* sp. 'Z-38.' The new variety was discovered in March 2006 by the inventor in a group of seedlings resulting from that crossing, in a commercial greenhouse in Moshav Mishmar Hashiva, Israel.

Asexual reproduction of the new cultivar 'DANOA35' by vegetative cuttings was first performed at a commercial greenhouse in Moshav Mishmar Hashiva, Israel in April 2006 and has shown that the unique features of this cultivar are stable and reproduced true to type in successive generations.

SUMMARY OF THE INVENTION

The cultivar 'DANOA35' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOA35' These characteristics in combination distinguish 'DANOA35' as a new and distinct *Calibrachoa* cultivar:

1. Unique bi-color flower color with a cream trumpet and a dark throat
2. Mounding plant habit.

Plants of the new cultivar 'DANOA35' are similar to plants of the seed parent, *Calibrachoa* sp. 'CV 738' in most horticultural characteristics, however, plants of the new cultivar 'DANOA35' have a mounding plant habit, compared to the trailing habit of 'CV-738.' Additionally, 'DANOA35' has different colored flowers than the seed parent.

Plants of the new cultivar 'DANOA35' are similar to plants of the pollen parent, *Calibrachoa* sp. 'Z-38 'in most horticultural characteristics, however, plants of the new cultivar 'DANOA35' have a mounding plant habit, compared to the trailing habit of 'Z-38.' Additionally, 'DANOA35' has slightly different colored flowers than the pollen parent.

Plants of the new cultivar 'DANOA35' are similar to plants of the commercial variety 'DANCALDARPINK,' U.S. Plant Pat. No. 17,029 in most horticultural characteristics, however, plants of the new cultivar 'DANOA35' have a mounding habit, whereas 'DANCALDARPINK' produces trailing plants. Additionally, 'DANCALARPINK' has pink flowers compared to the cream/orange flowers of 'DANOA35.'

BRIEF DESCRIPTION OF THE PHOTOGRAPH

Figure 1:
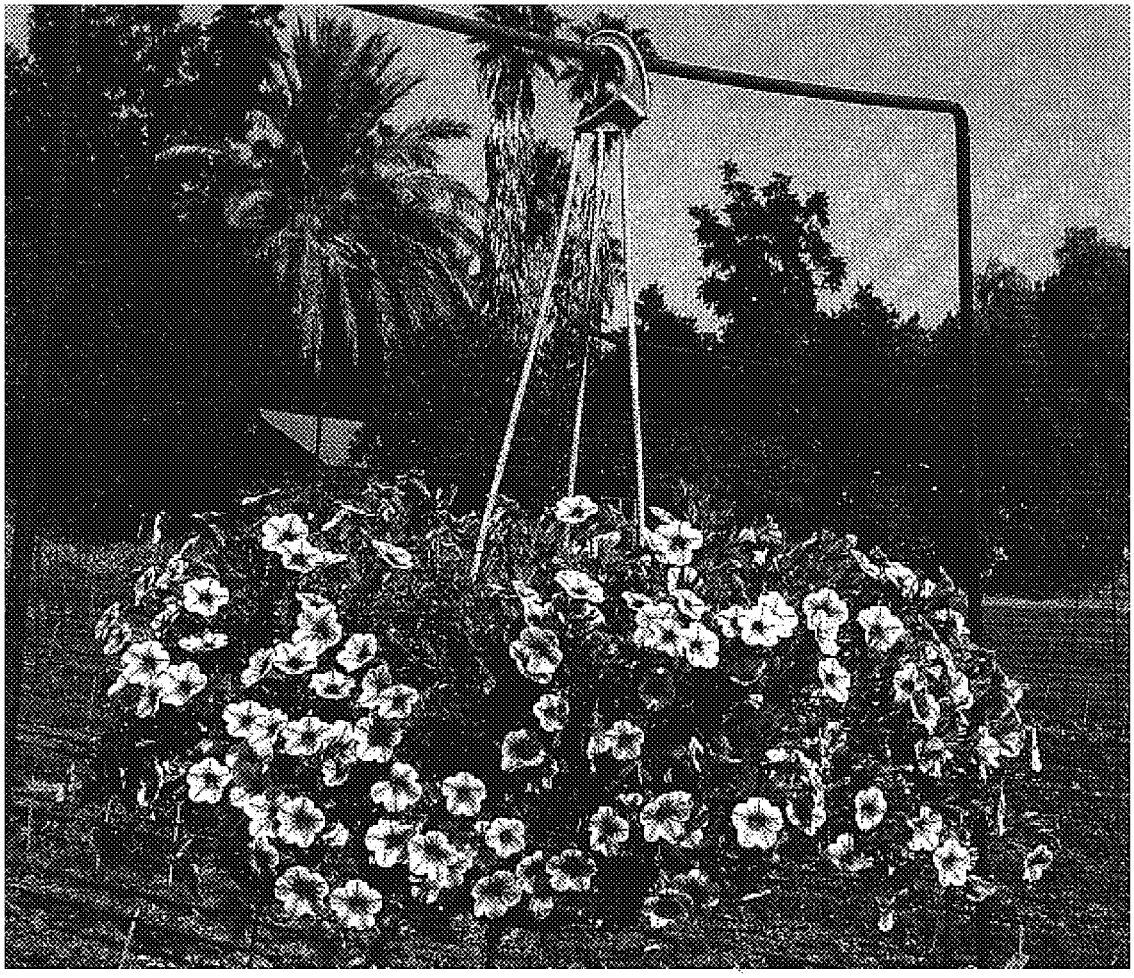

The accompanying photograph in FIG. 1 illustrates in full color a typical plant of 'DANOA35' grown in a greenhouse, in a 16 cm basket. Age of the plant photographed is approximately 90 days from a rooted cutting.

Figure 2:
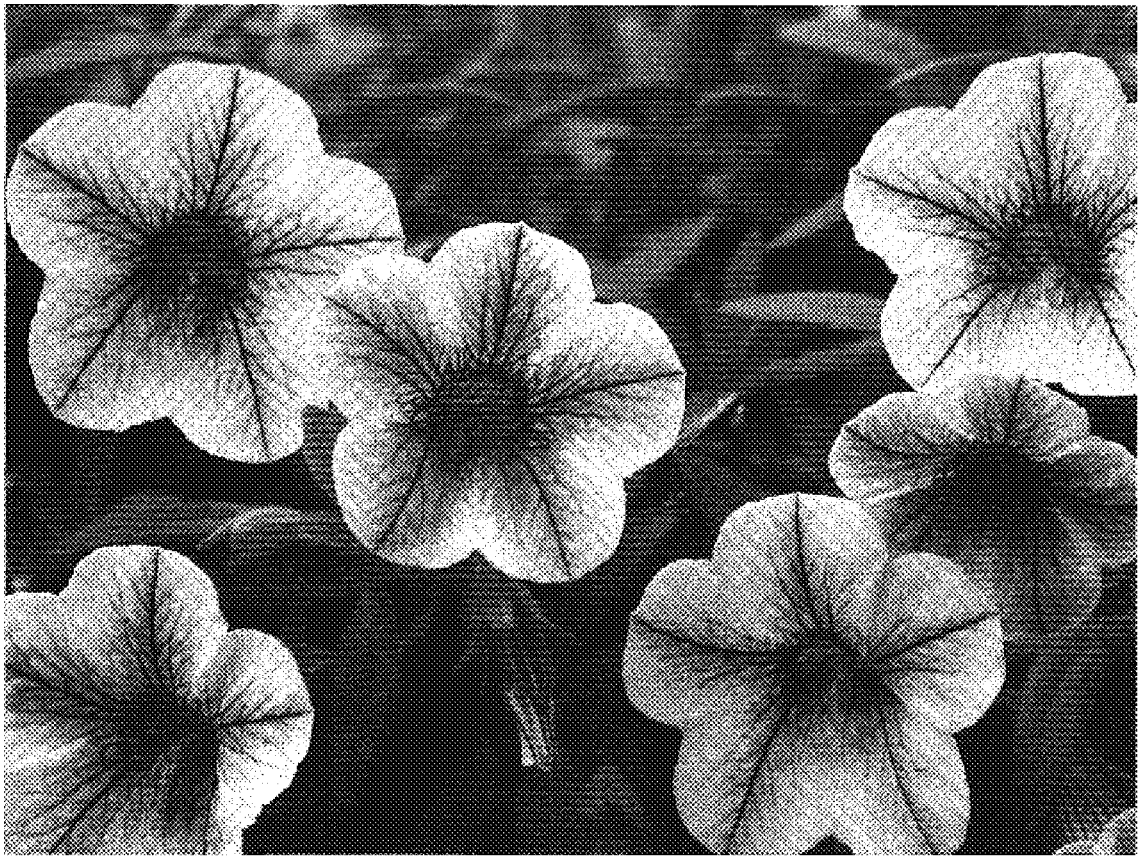

FIG. 2 illustrates in full color a close up of a typical bloom of 'DANOA35.'

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'DANOA35' plants grown in a greenhouse in Moshav Mishmar Hashiva, Israel. The growing temperature ranged from 18° C. to 24° C. The greenhouse is subject to partial shade. General light conditions are bright, normal sunlight, with some shade during the brightest part of the day. Measurements and numerical values represent averages of typical plant types.

Botanical classification: *Calibrachoa* sp. cultivar 'DANOA35.'

PROPAGATION

Time to initiate roots: About 8 days at approximately 25° C.
Time to develop roots: About 15 days at approximately 25° C.
Root description: Fine, fibrous.
Time to produce a rooted cutting: About 14 to 21 days at 25° C.

PLANT

Growth habit: Spreading annual.
Pot size of plant described: 12 cm.
Age of plant described: Approximately 80 days from a rooted cutting.
Height:
*To top of flowers*.—Approximately 30 cm.
Plant spread: Approximately 70 cm.
Growth rate: Vigorous.
Branching characteristics: Very well-branched. Branches from base of plant.
Length of primary lateral branches: Approximately 50 cm.
Diameter of lateral branches: Approximately 0.2 cm.
Quantity of primary lateral branches: About 60.
Characteristics of primary lateral branches:
*Form*.—Cylindrical.
*Diameter*.—Approximately 0.2 cm.
*Color*.—Near RHS Green 138B.
*Texture*.—Smooth.
Internode length: Approximately 2 cm.

FOLIAGE

Leaf:
*Arrangement*.—Alternate.
*Quantity*.—Dozens per branch.
*Average length*.—Approximately 2 cm.
*Average width*.—Approximately 0.5 cm.
*Shape of blade*.—Oblong.
*Apex*.—Rounded.
*Base*.—Acute.
*Margin*.—Entire.
*Texture of top surface*.—Puberulous.
*Aspect*.—Slanted upward 45 to 90°.
*Color*.—Young foliage upper side: Near RHS Green 137B. Young foliage under side: Near RHS Green 138B. Mature foliage upper side: Near RHS Green 137B. Mature foliage under side: Near RHS Green 138B.
*Venation*.—Type: Pinnate. Venation color upper side: Near RHS Green 137B. Venation color under side: Near RHS Green 138B.
*Petiole*.—None: Sessile.

FLOWER

Natural flowering season: Freely flowering all year in Moshav Mishmar Hashiva Israel. Begins flowering approximately 55 days after planting a rooted cutting.
Inflorescence and flower type and habit: Salverform, single with fused petals.
Rate of flower opening: Approximately 4 to 5 days from bud to fully opened flower.
Flower longevity on plant: Individual flowers last 4 to 5 days on the plant.
Quantity of flowers: Hundreds of flowers on each plant.
Flower size:
*Diameter*.—Approximately 2.5 cm.
*Length*.—Approximately 2.0 cm.
*Flower tube diameter at distal end*.—Approximately 1 cm.
*Flower tube diameter at proximal end*.—Approximately 0.2 cm.
Petals:
*Length from throat*.—About 1.3 cm.
*Width*.—About 1 cm.
*Quantity*.—5, fused.
*Texture*.—Glabrous.
*Apex*.—Obtuse.
*Margin*.—Entire.
Color:
*When opening*.—Upper surface: Near RHS White 155C with red veins. Lower surface: Near RHS White 155D with red veins.
*Fully opened*.—Upper surface: Near RHS White 155A with red veins. Lower surface: Near RHS White 155B with red veins. Flower throat (inside): Near RHS Yellow-Orange 14A Flower throat, vein: Near RHS Greyed-Orange 163B Flower tube (outside): Near RHS Greyed-Orange 163C Flower tube, vein: Near RHS Greyed-Orange 163C Petal color, fading to: Pure white, not on RHS.
Bud:
*Shape*.—Oblong.
*Length*.—Approximately 0.7 cm.
*Diameter*.—Approximately 0.2 cm.
*Color*.—Near RHS Yellow-Green 144B.
Calyx/Sepals:
*Quantity per flower*.—5, fused at base.
*Shape*. —Oblong.
*Length*.—Approximately 1.4 cm.
*Width*.—Approximately 0.7 cm.
*Apex*.—Obtuse.
*Base*.—Fused.
*Margin*.—Entire.
*Texture*.—Puberulous.
*Color*.—Upper Surface: Near RHS Yellow-Green 144A. Lower Surface: Near RHS Yellow-Green 144A.
Peduncle:
*Length*.—Approximately 2.5 cm.
*Diameter*.—Approximately 0.1 cm.
*Color*.—Near RHS Yellow-Green 146B.
*Orientation*.—Slanted upward at an angle of about 45°.
Fragrance: None.

REPRODUCTIVE ORGANS

Stamens:
*Number*.—5.
*Filament length*.—Approximately 0.6 cm.
Anthers:
*Length*.—Approximately 0.1 cm.
*Color*.—Near RHS Yellow 3A.
*Pollen*.—Color: Near RHS Yellow 3A. Quantity: Copious.
Pistil:
*Number*.—1.
*Length*.—Approximately 0.5 cm.

*Style*.—Length: Approximately 0.5 cm. Color: Near RHS Yellow-Green 154B.

*Stigma*.—Shape: Round. Color: Near RHS Gray-Green 197C. Ovary Color: Near RHS Yellow-Green 144B.

OTHER CHARACTERISTICS

Seeds and fruits: Not observed and not commercially important.

Disease/pest resistance: Neither resistance nor susceptibility to pathogens and pests common to *Calibrachoa* have been observed.

Temperature tolerance: The new variety tolerates temperatures between 8 to 35° C.

What is claimed is:

1. A new and distinct cultivar of *Calibrachoa* plant named 'DANOA35' as herein illustrated and described.

* * * * *